US010490303B2

(12) United States Patent
Sklar et al.

(10) Patent No.: US 10,490,303 B2
(45) Date of Patent: Nov. 26, 2019

(54) SYSTEMS AND METHODS FOR PATIENT HEALTH ASSESSMENT

(71) Applicant: Aetna Inc., Hartford, CT (US)

(72) Inventors: Aaron Sklar, Castro Valley, CA (US); Leonard Naar, London (GB); Brian Garcia, Redding, CT (US); Gregory B. Steinberg, Dingmans Ferry, PA (US)

(73) Assignee: Aetna Inc., Hartford, CT (US)

( * ) Notice: Subject to any disclaimer, the term of this patent is extended or adjusted under 35 U.S.C. 154(b) by 963 days.

(21) Appl. No.: 14/880,786

(22) Filed: Oct. 12, 2015

(65) Prior Publication Data

US 2016/0232328 A1 Aug. 11, 2016

Related U.S. Application Data

(63) Continuation-in-part of application No. 14/619,440, filed on Feb. 11, 2015, now abandoned.

(51) Int. Cl.
*G16H 10/60* (2018.01)

(52) U.S. Cl.
CPC .................. *G16H 10/60* (2018.01)

(58) Field of Classification Search
CPC .............................................. G06Q 50/22–24
See application file for complete search history.

(56) References Cited

U.S. PATENT DOCUMENTS

| 7,169,085 | B1 * | 1/2007 | Killin | G06F 19/3481 |
| | | | | 482/8 |
| 8,337,409 | B2 * | 12/2012 | Iliff | G06F 19/325 |
| | | | | 600/483 |
| 9,305,059 | B1 * | 4/2016 | Glickman | G06F 16/2457 |
| 2002/0035486 | A1 * | 3/2002 | Huyn | G06F 19/3418 |
| | | | | 705/3 |
| 2007/0202483 | A1 * | 8/2007 | Castelli | G09B 3/00 |
| | | | | 434/350 |
| 2008/0086336 | A1 | 4/2008 | Hertel et al. | |
| 2008/0162182 | A1 | 7/2008 | Cazares et al. | |
| 2009/0007924 | A1 * | 1/2009 | Iliff | G06F 19/3418 |
| | | | | 128/898 |

(Continued)

OTHER PUBLICATIONS

International Patent Application No. PCT/US2016/017542, Search Report (dated Apr. 22, 2016).

*Primary Examiner* — Robert A Sorey
(74) *Attorney, Agent, or Firm* — Leydig, Voit & Mayer, Ltd.

(57) ABSTRACT

A system and method including: receiving medical data related to a patient; identifying two or more assessments to be performed by a case manager based on the medical data, each including a different set of questions to be answered by the patient, and each set of questions is directed to a different medical condition that the patient is at risk of having based on the medical data; prioritizing the two or more assessments based on the medical data and additional input from the case manager; displaying, in a user interface of a case manager terminal, a listing of questions from the highest priority assessment; receiving a response to a first question; reprioritizing the two or more assessments based on the response; and, displaying, in the user interface, a listing of unanswered questions from the set of questions included in the assessment having the highest priority based on the reprioritizing.

9 Claims, 16 Drawing Sheets

(56) References Cited

U.S. PATENT DOCUMENTS

| | | | |
|---|---|---|---|
| 2011/0161107 A1* | 6/2011 | Goldberg | G06F 19/3418 |
| | | | 705/3 |
| 2011/0295619 A1 | 12/2011 | Tough | |
| 2014/0108037 A1* | 4/2014 | Plummer | G06Q 10/10 |
| | | | 705/2 |
| 2014/0114680 A1 | 4/2014 | Mills et al. | |
| 2014/0122109 A1* | 5/2014 | Ghanbari | G06F 19/345 |
| | | | 705/2 |
| 2014/0214441 A1 | 7/2014 | Young et al. | |
| 2014/0289161 A1* | 9/2014 | Johnson | G06Q 30/0631 |
| | | | 705/347 |
| 2014/0324467 A1 | 10/2014 | Hayes | |
| 2014/0342333 A1 | 11/2014 | Knoche et al. | |
| 2015/0216413 A1* | 8/2015 | Soyao | A61B 5/0022 |
| | | | 709/204 |
| 2015/0332021 A1* | 11/2015 | Godla | G16H 10/20 |
| | | | 705/3 |

\* cited by examiner

SYSTEMS AND METHODS FOR PATIENT HEALTH ASSESSMENT

CROSS-REFERENCE TO RELATED APPLICATIONS

This application is a continuation-in-part of U.S. patent application Ser. No. 14/619,440, filed on Feb. 11, 2015, which is hereby incorporated by reference herein in its entirety.

FIELD

This disclosure relates generally to the field of health care management and, more specifically, to systems and methods for patient health assessment.

BACKGROUND

In conventional systems for patient health assessment, a case manger, such as a registered nurse or nurse practitioner, may contact a patient (e.g., by telephone) to perform one or more "assessments" on the patient. In conventional systems, an assessment includes a predefined series of questions to be asked to the patient. Some assessments are "linear," meaning that the questions are asked in a certain order. The case manger typically asks the patient each question in order to solicit a response from the patient. Once all of the questions for an assessment have been answered, the assessment is deemed to be completed. The completed assessment can then be used by the case manager or other medical professionals to provide a care plan for the patient. In some instances, the case manager may have multiple assessments to complete with a patient.

However, a problem exists with conventional case manager assessments when the patient interrupts the linear question list of an assessment to provide unrelated information or to ask his or her own questions to the case manager. Such events can derail an assessment and may cause confusion and unnecessary delays in completing the assessment. Because the assessment process is lengthened, patients can get frustrated with the process and may perceive the case manager as simply reading from a script and not actually caring about the patient's well-being. Case managers are often left with incomplete assessments and an array of notes to reconcile through data entry after a communications session is completed with the patient. As such, the conventional approach to case manager assessments is time-consuming and error-prone for the case manager, which may result in inadequate medical care provided to the patient.

Accordingly, there remains a need for systems and methods for patient health assessment that overcome the drawbacks and limitations of current approaches.

SUMMARY

Embodiments of the disclosure provide systems and methods for patient health assessment. In one embodiment, a system includes a clinical data database and a case manager terminal computing device executing one or more processors for performing a patient health assessment. The case manager terminal computing device is configured to perform the step of: receiving, from a calculation engine module executing on a health organization server computing device, medical data related to the patient that is stored in the clinical data database; identifying one or more assessments to be performed by a case manager for the patient, wherein each assessment includes one or more questions to be answered by the patient; displaying, in a user interface on a display device, visual indicators that indicate a level of completeness of each of the one or more assessments; displaying in the user interface a listing of questions to be asked to the patient for a current assessment; receiving in a data input field included in the user interface, input data from the case manager; and in response to the input data, displaying in the user interface an updated listing of questions to be asked to the patient, wherein the updated listing of questions includes one or more questions that, when answered by the patient, advance the progress of completion of at least one of the one or more assessments. The health organization server computing device can be associated with a health insurance company or a health care provider, for example.

Another embodiment of disclosure provides a computer-readable storage medium, system, or method for performing assessments that includes: receiving, from a calculation engine module executing on a server computing device, data related to a person that is stored in a database; identifying one or more assessments to be performed for the person, wherein each assessment includes one or more questions to be answered by the person; displaying, in a user interface on a display device of an assessor terminal computing device, visual indicators that indicate a level of completeness of each of the one or more assessments; displaying, in the user interface, a listing of questions to be asked to the person for a current assessment; receiving, in a data input field included in the user interface, input data from the assessor; and, in response to the input data, displaying in the user interface an updated listing of questions to be asked to the person, wherein the updated listing of questions includes one or more questions that, when answered by the person, advance the progress of completion of at least one of the one or more assessments.

Yet another embodiment includes a method comprising: receiving, from a calculation engine module executing on a health organization server computing device, medical data related to a patient that is stored in a clinical data database, wherein the medical data includes at least claims data and lab results data for the patient; identifying two or more assessments to be performed by a case manager for the patient based on the medical data, wherein each of said two or more assessments includes a different set of questions to be answered by the patient, and each set of questions is directed to a different medical condition that the system identifies the patient is at risk of having based on the medical data; prioritizing the two or more assessments based on the medical data and additional input from the case manager; displaying, in a user interface of a case manager terminal, a listing of questions from the set of questions included in the assessment having the highest priority based on the prioritizing; receiving a response to a first question from the set of questions; reprioritizing the two or more assessments based on the response; and, displaying, in the user interface, a listing of unanswered questions from the set of questions included in the assessment having the highest priority based on the reprioritizing.

Yet another method includes: receiving, from a calculation engine module executing on a health organization server computing device, medical data related to a patient and stored in a clinical data database, wherein the medical data includes one or more of medication data, claims data, and lab results data for the patient; from the medical data, identifying plural assessments corresponding to a respective one of plural identified medical conditions, each of said assessments including a set of questions tailored to the respective one of the plural medical conditions; performing a weighted analysis of the medical data by the calculation engine module, and, based on the analysis, prioritizing said assessments and questions therein; and selecting a top prioritized assessment, and a top prioritized question therein, for presentation by the case manager and response by the patient; and wherein the system is further capable of performing the steps of: (i) displaying, in an electronic display device, the selected question from the selected assessment, for presentation by the case manager and response by the patient; (ii) electronically receiving a response from the patient to the displayed question, wherein the response from the patient is directed to one of the plural identified medical conditions, a further medical condition, and/or an assessment prioritization preference; and based on both the medical data and the received response: (a) identifying a further assessment corresponding to a further medical condition identified in the response; (b) reprioritizing each of said assessments and questions therein, based on a weighted analysis of both the medical data and the received response; and (c) selecting a top prioritized uncompleted assessment, and a top prioritized unanswered question therein; and (iii) repeating steps (i)-(ii).

DETAILED DESCRIPTION

Embodiments of the disclosure provide systems and methods for conducting patient health assessments. According to the embodiment disclosed herein, a starting point (i.e., a question) for a case manager (also referred to as an "assessor") to begin an assessment is suggested by to the case manager by a computer system. For example, the case manager may be using a computer that is executing software that provides the suggestion to the case manager. In other implementations, a software module executing on another computer system performs the analysis to determine which question to begin the assessment. While the assessment is taking place, the computer system dynamically changes the order of the questions depending on the patient's last statement. The computer system can also provide follow up questions depending on the patient's last statement. The computer system also allows the case manager to search for questions related to the topic of the conversation.

Accordingly, embodiments of the disclosure empower the case manager to use their professional judgment to choose which question to ask next to the patient. This allows the direction of the conversation to drive the order of questions, enabling the ability to fluidly switch from one set of assessment questions to a completely separate set of questions, depending on the flow of the conversation. A level of completeness of each assessment can also be visually represented on a display device of the computer system operated by the case manager, which enables the case manager to effortlessly access various assessments to view remaining questions.

Figure 1:
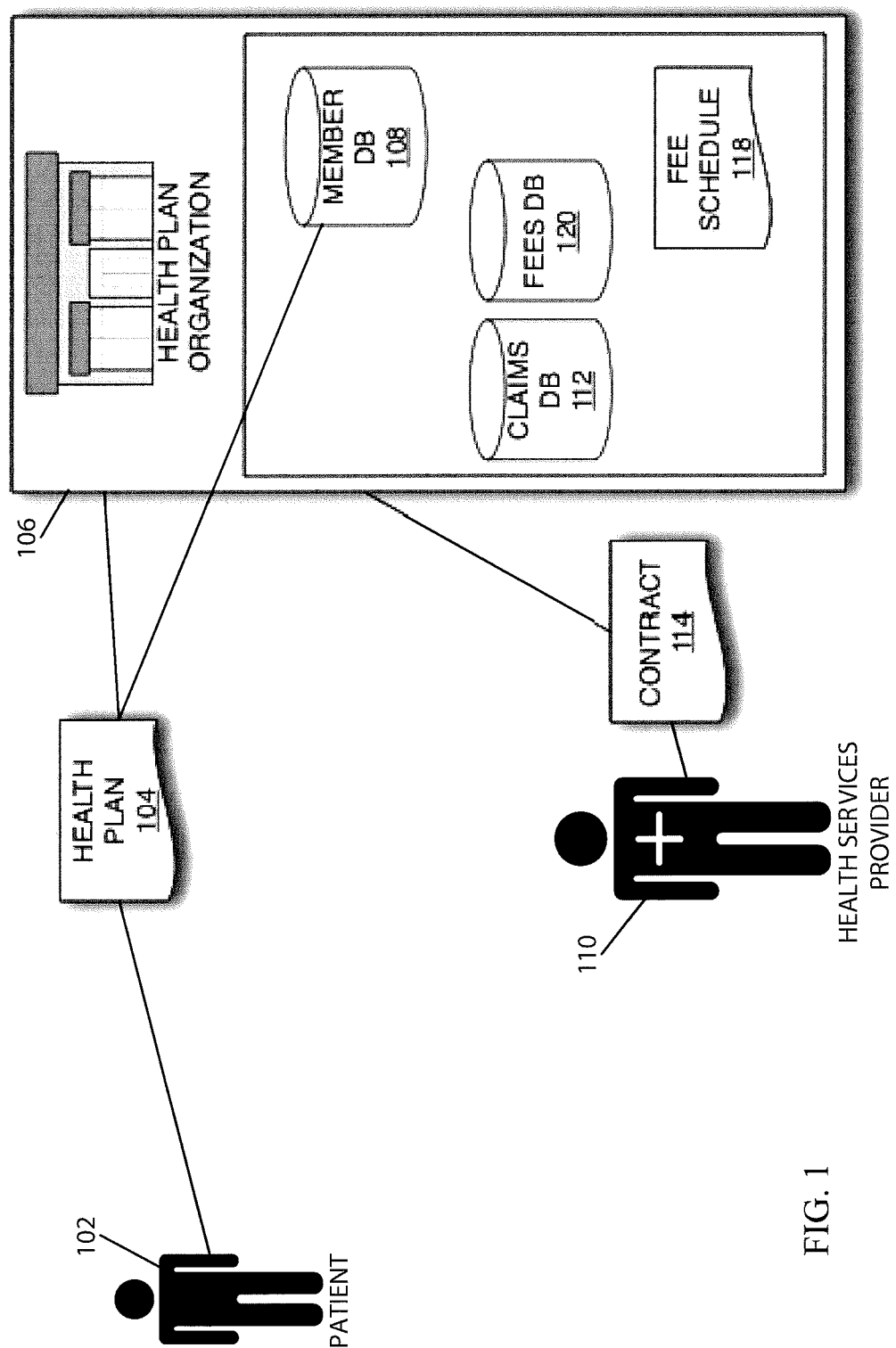
FIG. 1 is a conceptual diagram of a system with reference to an overall healthcare environment, according to one embodiment.

Turning to FIG. 1, an implementation of a system contemplated by an embodiment of the disclosure is shown with reference to an overall healthcare environment, according to one embodiment. A patient (also referred to as a "subscriber" or "member" or "consumer") 102 is a member of a health plan 104 of a health plan organization ("HPO") 106. The patient 102 may subscribe to the health plan 104 through, for example, his or her employer. Alternatively, the patient 102 may obtain benefits of the health plan 104 through a subscriber (e.g., a spouse or child of a subscriber can be a member of a health plan). The HPO 106 can be a health insurance company and the health plan 104 can be one of a number of health insurance or related products, such as a PPO (Preferred Provider Organization), HMO (Health Maintenance Organization), POS (Point-of-Service), or the like. The health plan 104 can also be a consumer-directed health plan, such as a high deductible health plan, health reimbursement arrangement (HRA), health savings account (HSA), or the like. The patient's health plan 104 covers various health care services according to one of a variety of pre-arranged terms. Details for the patient 102 and the corresponding plan 104 are stored in a member database 108. The terms of the plan 104 can vary greatly from plan to plan according to (among other things): what types of services are provided, where the services are provided, by whom they are provided, the extent to which the patient is personally responsible for payment, amount of deductibles, etc. Generally, however, regardless of the specific plan subscribed to, when a patient 102 obtains health care services from a provider 110, either the patient 102 or the provider 110 can submit a claim to the HPO 106 for reimbursement or payment. For analysis purposes, historical claim data is stored in a claims database 112.

A health care services provider 110 may have a contractual relationship 114 with the HPO 106. Under the contract 114, the provider 110 typically agrees to provide services to members 102 of the HPO 106 at scheduled rates. The rates are stored in a fee schedule 118, preferably stored in a fees database 120 maintained by the HPO 106. By contracting with the HPO 106, the provider 110 generally increases the amount of business the provider 110 receives from members 102, and members 102 generally receive a less expensive rate than they would otherwise receive for a health service provided by the provider 110. The actual amount of out-of-pocket expense to be paid by a patient 102 may vary according to the terms of his health plan 104 (e.g., co-payments, co-insurance or deductibles may apply), but will generally be at most the contracted rate.

Figure 2:
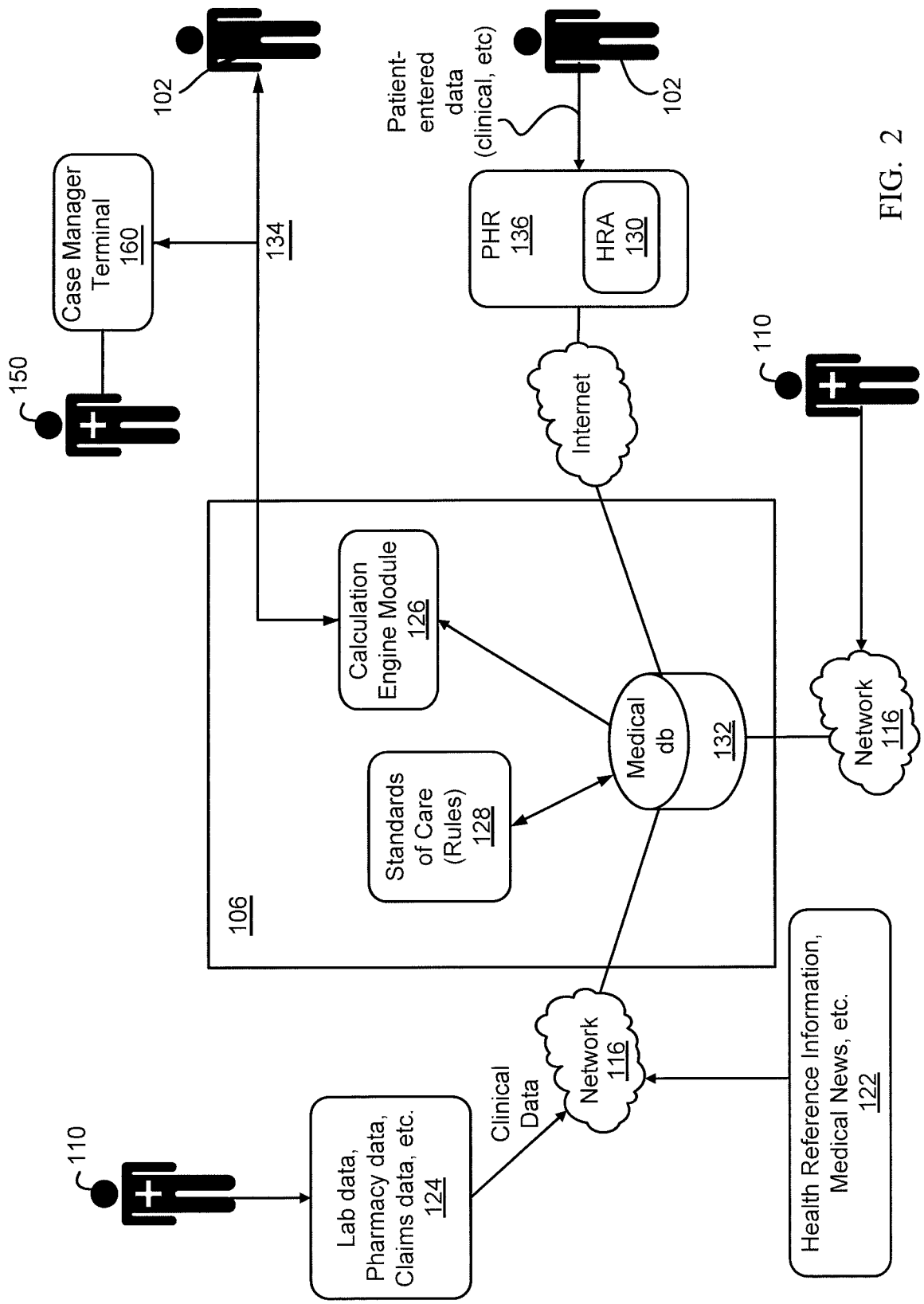
FIG. 2 is a schematic diagram illustrating an overview of a system for communicating with a health plan member, according to one embodiment.

FIG. 2 is a schematic diagram illustrating an overview of a system for communicating with a health plan member (e.g., patient 102), according to one embodiment. A health plan organization 106 collects and processes a wide spectrum of medical care information relating to a patient 102 in order to attempt to mitigate risk of the patient 102. A personal health record (PHR) 136 of a patient 102 may be configured to solicit the patient's input for entering additional pertinent medical information, tracking follow-up actions, and allowing the health plan organization 106 to track the patient's medical history. In some embodiments, the medical care information relating to the patient can include health risk appraisal (HRA) information, also referred to as a health risk appraisal, or health and well-being questionnaire. In one embodiment, the HRA is a questionnaire used to gather the pertinent medical information from the patient 102.

When the patient 102 utilizes the services of one or more health care providers 110, a medical insurance carrier collects the associated clinical data 124 in order to administer the health insurance coverage for the patient 102. Additionally, a health care provider 110, such as a physician or nurse, can enter clinical data 124 into one or more health care provider applications pursuant to a patient-health care provider interaction during an office visit or a disease management interaction. Clinical data 124 originates from medical services claims, pharmacy data, as well as from lab results, and includes information associated with the patient-health care provider interaction, including information related to the patient's diagnosis and treatment, medical procedures, drug prescription information, in-patient information, and health care provider notes, among other things. The medical insurance carrier and the health care provider 110, in turn, provide the clinical data 124 to the health plan organization 106, via one or more networks 116, for storage in one or more medical databases 132. The medical databases 132 are administered by one or more server-based computers associated with the health plan organization 106 and comprise one or more medical data files located on a computer-readable medium, such as a hard disk drive, a CD-ROM, a tape drive, or the like. The medical databases 132 may include a commercially available database software application capable of interfacing with other applications, running on the same or different server based computer, via a structured query language (SQL). In an embodiment, the network 116 is a dedicated medical records network. Alternatively, or in addition, the network 116 includes an Internet connection that comprises all or part of the network.

In some embodiments, an on-staff team of medical professionals within the health plan organization 106 consults various sources of health reference information 122, including evidence-based preventive health data, to establish and continuously or periodically revise a set of clinical rules 128 that reflect best evidenced-based medical standards of care for a plurality of conditions. The clinical rules 128 are stored in the medical database 132.

To supplement the clinical data 124 received from the insurance carrier, the PHR 136 and/or an HRA questionnaire allow patient entry of additional pertinent medical information that is likely to be within the realm of patient's knowledge. Examples of patient-entered data include additional clinical data, such as patient's family history, use of non-prescription drugs, known allergies, unreported and/or untreated conditions (e.g., chronic low back pain, migraines, etc.), as well as results of self-administered medical tests (e.g., periodic blood pressure and/or blood sugar readings). Preferably, the PHR 136 facilitates the patient's task of creating a complete health record by automatically populating the data fields corresponding to the information derived from the medical claims, pharmacy data, and lab result-based clinical data 124. In one embodiment, patient-entered data also includes non-clinical data, such as upcoming doctor's appointments. In some embodiments, the PHR 136 gathers at least some of the patient-entered data via a health risk assessment tool (HRA) 130 that requests information regarding lifestyle, behaviors, family history, known chronic conditions (e.g., chronic back pain, migraines, etc.), and other medical data, to flag individuals at risk for one or more predetermined medical conditions (e.g., cancer, heart disease, diabetes, risk of stroke, etc.) pursuant to the processing by a calculation engine module 126, which a software module executed by one or more processors included in a computer system. Preferably, the HRA 130 presents the patient 102 with questions that are relevant to his or her medical history and currently presented conditions. The risk assessment logic branches dynamically to relevant and/or critical questions, thereby saving the patient time and providing targeted results. The data entered by the patient 102 into the HRA 130 also populates the corresponding data fields within other areas of PHR 136. The health plan organization 106 aggregates the clinical data 124 and the patient-entered data, as well as the health reference and medical news information 122, into the medical database(s) 132 for subsequent processing via a calculation engine module 126.

The health plan organization 106 includes a multi-dimensional analytical software application including a calculation engine module 126 comprising computer-readable instructions for performing analysis on the contents of the medical databases 132 in order to attempt to mitigate risk of the patient 102. In some embodiments, a patient is stratified into one of three risk tiers, including a high risk tier, a moderate risk tier, and a low risk tier. Based on the risk tier of a patient and other engagement factors, the health plan organization can reach out to the patient 102 via communications medium 134. Example communications media 134 include telephone, postal mail, email, text message, or other electronic or non-electronic communication media. In various embodiments, the type of communication medium 134 used to reach out to or "engage" the patient 102 depends on the risk tier and/or other engagement factors. Also, the communication medium 134 allows data transfer between the calculation engine module 126 and the case manager terminal 160 operated by a case manager 150. In some examples, the case manager 150 is a registered nurse or nurse practitioner. In some embodiments, the calculation engine module 126 is included in the case manager terminal 150.

For example, a case manager 150 may be notified that a patient 102 is the highest-risk tier and/or that the patient has received a poor lab result, via the case manager terminal 160. This notification is received by the case manager terminal 160 from the calculation engine module 126.

The case manager 150 may initiate a communications session with the patent 102 via the communications medium 134, such as by placing a phone call to the patient. One goal of the case manager's interaction with the patient may be to identify the cause of a health problem with the patient 102. This can be done by performing one or more "assessments" on the patients. In some embodiments, an assessment includes a series of questions to be asked to the patient. Some assessments may be "linear," meaning that the questions should be asked in a certain order. In some embodiments, the case manager 150 is provided with multiple recommended assessments to complete with a given patient 102.

However, as described above, a problem exists with conventional case manager assessments when the patient interrupts the linear question list of an assessment to provide unrelated information or to ask his or her own questions to the case manager. Such events can derail an assessment and may cause confusion and unnecessary delays in completing the assessment. Because the assessment process is lengthened, patients can get frustrated with the process and may perceive the case manager as simply reading from a script and not actually caring about the patient's well-being. Case managers are often left with incomplete assessments and an array of notes to reconcile through data entry after a communications session is completed with the patient. As such, the conventional approach to case manager assessments is time-consuming and error-prone for the case manager, which may result in inadequate medical care provided to the patient.

Accordingly, embodiments of the disclosure provide for improved systems and methods for patient health assessment. According to various embodiments, a case manger 150 opens a computer program on the case manager terminal 160 to begin a new encounter with a patient 102. A visual dashboard or user interface is displayed on a display screen of the case manager terminal 160 that includes a listing of assessments that are incomplete for the patient 102, where each assessment includes one or more questions to be answered by the patient 102. For each assessment, a visual indicator is displayed that indicates a level of completeness of the assessment (e.g., 0% complete, 25% complete, 100% complete, 3 of 10 questions answered, etc.).

The case manger 150 begins by asking a question for one of the assessments that has not yet been answered. The initial question may be part of a "current assessment" and an initial set of questions to ask the patient from the current assessment may be provided to the case manager terminal 160 based on analysis performed by the calculation engine module 126. In some embodiments, the calculation engine module 126 is part of the case manager terminal 160. In other embodiments, the calculation engine module 126 is in a separate computer system than the case manager terminal 160, such as in a server of a health plan organization 106. In some embodiments, the current assessment may be selected for the initial set of questions based on the medical data for the patient and a corresponding severity of the condition associated with the assessment.

When the patient 102 answers a question, the answer is recorded against the assessments that include that question, such as the current assessment (and any other assessments that also include the question that was asked). One or more recommended questions from the current assessment may then be prompted to the case manger 150 to ask the patient 102 (based on analysis performed by the calculation engine module 126). Also, in some embodiments, the answer to the first question may cause the calculation engine module 126 to select a different assessment as the "current assessment." For example, the answer to the first question may raise the priority level of a different assessment based on a severity of the condition associated with the answer to the first question. As such, a top prioritized assessment, and a top prioritized question therein, are selected for presentation by the case manager and response by the patient. This process of asking questions, receiving answers, which can be electronically entered automatically by a computing system or by the case manager, and reprioritizing assessments and/or questions to ask continues until the patient 102 begins to get off-track, meaning that the patient 102 begins to provide unsolicited information about things that the case manger 150 has not asked that may or may not be relevant to the assessments that are yet to be completed.

In some embodiments, a data input field may be in displayed on the case manager terminal 160 that allows the case manger 150 to search for related question to the patient conversation, e.g., in situations where the patient 102 has taken the conversation off-course. Based on the input in the data input field, the case manager terminal 160, in conjunction with the calculation engine module 126, may provide new recommendations for questions from one or more other assessments besides the current assessment to keep the conversation relevant to the present topic and to carry on with the progress of completing the assessments. As the new questions are asked and answered, progress is made towards completing multiple assessments in parallel while keeping the conversation relevant to topics that the patient 102 is interested in discussing.

Also, in some embodiments, the calculation engine module 126 may identify a particular assessment and/or question to ask the patient based on unsolicited information from the patient and/or medical data. For example, the patient may indicate to the case manager that he or she is busy and has only five minutes to talk to the case manager. The case manager can the input this time restriction into the user interface of the case manager terminal. The calculation engine module 126 may then prioritize the assessments and/or questions to ask the patient based on the amount of that the patient has to talk to the case manager. In one embodiment, the medical data related to a patient and stored in the clinical data database, where the medical data includes one or more of medication data, claims data, and lab results data for the patient. In one embodiment, the medical data includes each of medication data, claims data, and lab results data. In another embodiment, medication data alone is used as an alternative to claims data and lab results data.

Another example of unsolicited input from the patient includes information about which particular condition the patient wishes to talk about. For example, suppose the patient is at risk for each of (i) heart disease, (ii) migraines, and (iii) in-grown toenails. A separate assessment is recommended by the calculation engine module 126 for each of the conditions (i)-(iii). The calculation engine module 126 may also determine heart disease is the most severe of these conditions and may identify the heart disease assessment as the initial assessment for the case manager to begin the session with the patient. However, although arguably less severe of a condition, the in-grown toenails are very much bothering the patient at the moment. In this example scenario, the case manager may start by asking a question from the heart disease assessment. In response, the patient may say that he or she is not interested in talking about heart disease and would rather talk about the in-grown toenail problem that the patient is having. The case manager may input this response into the case manager terminal, to which the calculation engine module 126 may prioritize the in-grown toenail assessment and prompt the case manager to ask questions from the in-grown toenail assessment.

While the entity relationships described in FIG. 2 are representative, those skilled in the art will realize that alternate arrangements are possible. In one embodiment, for example, the health plan organization 106 and the medical insurance carrier are the same entity. Alternatively, the health plan organization 106 is an independent service provider engaged in collecting, aggregating, and processing medical care data from a plurality of sources to provide a personal health record (PHR) service for one or more medical insurance carriers. In yet another embodiment, the health plan organization 106 provides PHR services to one or more employers by collecting data from one or more medical insurance carriers. In yet another implementation, case manager terminal 160 is part of health plan organization 106.

Figure 3:
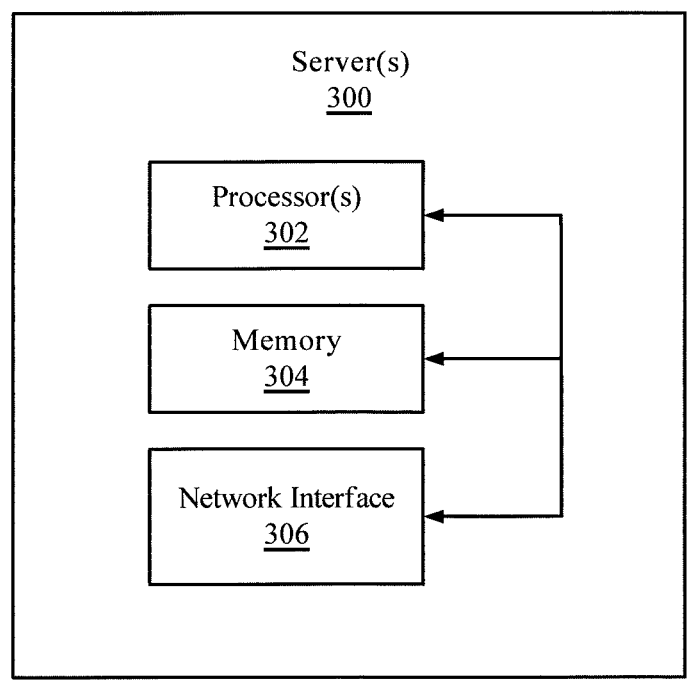
FIG. 3 is a block diagram of basic functional components for a server or cluster of servers configured to implement embodiments of the disclosure.

FIG. 3 is a block diagram of basic functional components for a server or cluster of servers configured to implement embodiments of the disclosure. For example, server 300 may represent the computer system that executes the calculation engine module 126 and/or case manager terminal 160 shown in FIG. 2. In some embodiments, server 300 is configured to be a computer or computers operated by an insurance carrier and/or case manager.

The server 300 includes one or more processors 302, memory 304, and network interface 306. In some embodiments, each of the components including the processor(s) 302, memory 304, and network interface 306 is interconnected physically, communicatively, and/or operatively for inter-component communications.

As illustrated, processors 302 are configured to implement functionality and/or process instructions for execution within server 300. For example, processors 302 execute instructions stored in memory 304. Memory 304, which may be a non-transient, computer-readable storage medium, is configured to store information within server 300 during operation. In some embodiments, memory 304 includes a temporary memory, i.e., an area for information not to be maintained when the server 300 is turned off. Examples of such temporary memory include volatile memories such as random access memories (RAM), dynamic random access memories (DRAM), and static random access memories (SRAM). Memory 304 also maintains program instructions for execution by the processors 302.

The server 300 uses network interface 306 to communicate with external devices via one or more networks, such as the network 116 in FIG. 1. Network interface 306 may also provide a phone or Internet-enabled voice and/or video connection between a case manager and a patient. Such networks may include one or more cellular networks, wireless networks, wired networks, fiber optics networks, and other types of networks through which communication between the server 300 and an external device may be established. Network interface 306 may be a network interface card, such as an Ethernet card, an optical transceiver, a radio frequency transceiver, or any other type of device that can send and receive information.

Figure 4:
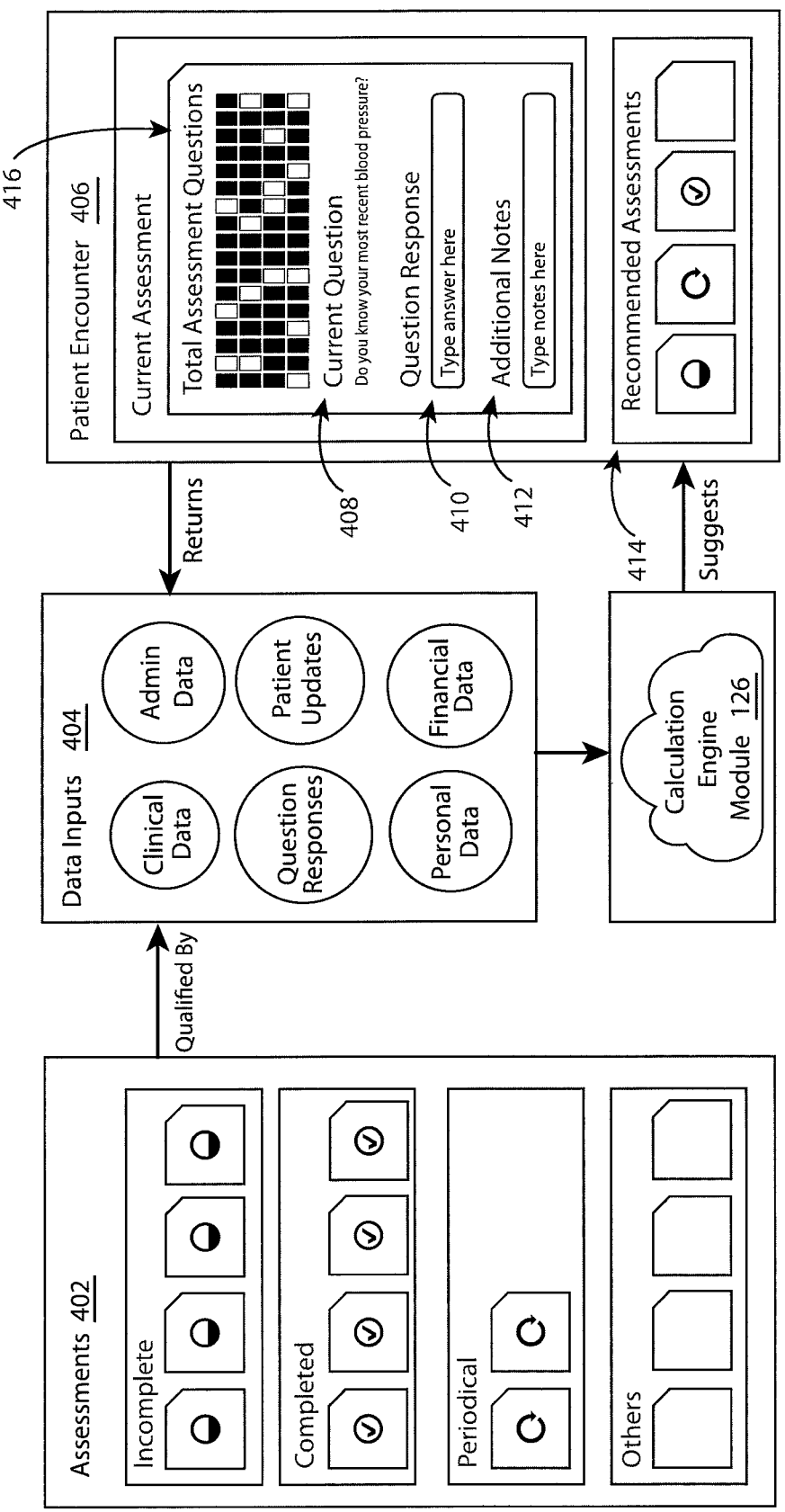
FIG. 4 is a conceptual diagram illustrating non-linear assessments, according to one embodiment.

FIG. 4 is a conceptual diagram illustrating non-linear assessments, according to one embodiment. As shown in FIG. 4, various assessments 402 can be associated with a particular patient based on or quantified by data inputs 404 for the patient. Example data inputs 404 include clinical data, administrative data, question responses, patient updates, personal data, financial data, among others, that are stored in a medical database. As shown in FIG. 4, the assessments 402 can be categorized as incomplete, completed, periodical, or others. As described, each assessment includes one or more questions to be answered by the patient. When all the questions of an assessment are answered, the assessment is deemed "completed." If at least one question remains unanswered, then the assessment is deemed "incomplete." A "periodical" assessment, in some embodiments, is an assessment that should be administered to the patient on a periodic basis, e.g., once a year.

When a case manger 150 logs into a case manager terminal 160 to begin a patient encounter 406, a user interface is displayed on the case manager terminal 160 to the case manager 150. The user interface may provide visual indications of which assessments are recommended to complete 414 and may provide a recommendation 408 of a question to ask the patient. For example, the selection of the current assessment and the recommended question 408 may be based on the severity of the condition associated with the current assessment as it relates to the patient's medical data. A data input field 410 may also be provided in the user interface to allow input by the case manager, e.g., of a patient response to a question that is off-topic. The data input field 410 may be a text field, a drop-down selection menu, radio button selection menu, or checkbox-based menu choices, among others. A notes section 412 of the user interface may provide an input field where the case manager can input additional notes about the answer to the question.

When a patient answers a question, the data is transmitted from the case manager terminal 160 to be stored in a database as data inputs 404 (e.g., database 132 in FIG. 2) and is used by a calculation engine module (e.g., calculation engine module 126 in FIG. 2) to generate a new question recommendation 408. The recommendation may be part of the same assessment as the previous question or from a different assessment.

Another user interface feature may include a table 416 of all questions for the recommended assessments 414, with one visual indicator indicting that a particular question has been answered and another visual indication indicating that a particular question has not been answered. For example, the visual indications may be different colors for questions that been answered and questions that have not been answered.

According to some embodiments, the assessments can be completed in a non-linear manner in which questions from different assessments can be asked to the patient based on, for example, the flow of the conversation, as described in greater detail herein. Also, in some embodiments, the assessments are selected based on unsolicited input from the patient, such as an amount of time that the patient has to talk to the case manager and/or a particular condition that the patient wishes to discuss.

Figure 5:
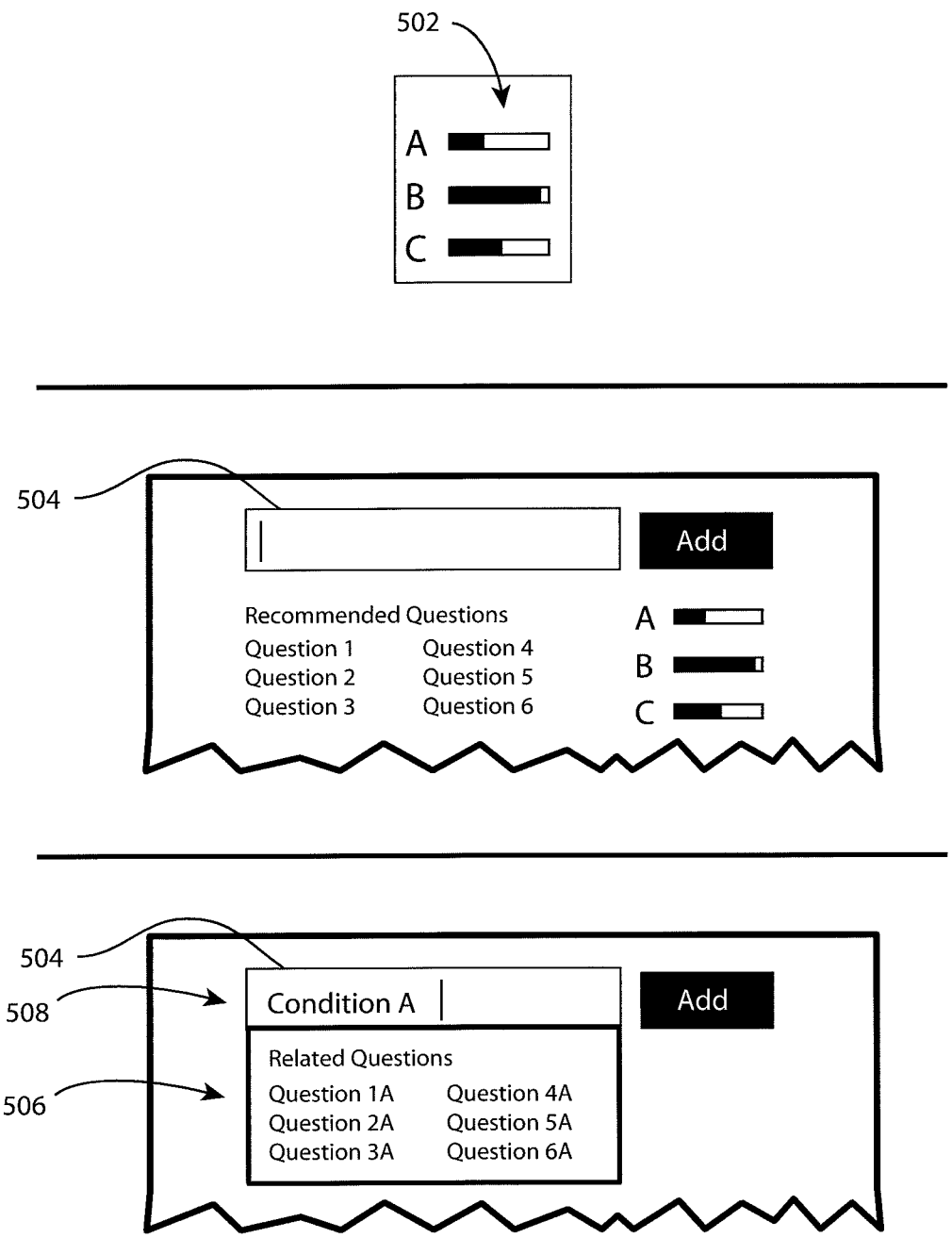
FIG. 5 is a conceptual diagram illustrating non-linear assessments and a data input field for searching for questions to ask, according to one embodiment.

FIG. 5 is a conceptual diagram illustrating non-linear assessments and a data input field 504 for searching for questions to ask at patient, according to one embodiment. As shown in FIG. 5, when a case manager opens a new patient encounter, a visual indicator 502 may be displayed in a user interface showing which recommended assessments are to be completed. In the example in FIG. 5, three assessments "A," "B," and "C" are yet to be completed. A fill-bar visual indicator 502 is shown in FIG. 5, where the fill-bar is increased when a question for a particular assessment has been asked and answered until the fill-bar is full, which indicates that the assessment has been completed.

The user interface may also include a data input field 504 for searching for questions to ask the patient. In one example scenario, suppose the case manager asked a particular question to the patient. The patient, instead of answering the question, provides some other information that does not answer the question that was asked. The case manager can input the other information provided by the patient (e.g., "Condition A" in FIG. 5) in the data input field 504. The other information is transmitted back to the calculation engine module 126 that processes the information to generate a listing 506 of recommended questions (e.g., Questions 1A-6A in FIG. 5) to ask the patient based on the other information that was provided in the data input field 504. The questions in the listing 506 may questions that are need to complete the remaining assessments for the patient, but are also relevant to the flow of the conversation. As such, as questions are asked and answered, progress is made towards completing multiple assessments in parallel. Each question answered in the non-linear assessment may prompt follow-on questions to further satisfy the assessment requirements.

Figure 6:
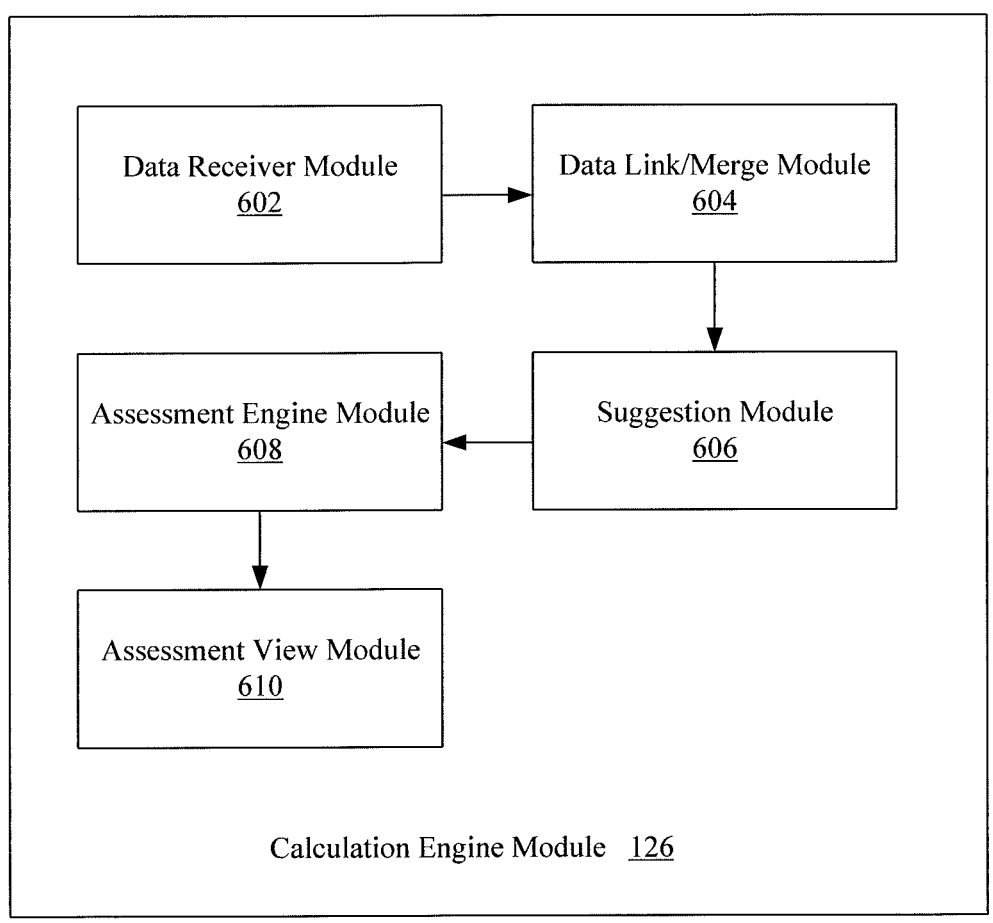
FIG. 6 is a conceptual diagram illustrating software modules included in a calculation engine module to provide non-linear assessments, according to one embodiment.

FIG. 6 is a conceptual diagram illustrating software modules included in a calculation engine module 126 to provide non-linear assessments, according to one embodiment. As shown, the calculation engine module 126 includes a data receiver module 602, a data link/merge module 604, a suggestion module 606, an assessment engine module 608, and an assessment view module 610. Each of the modules in FIG. 6 may be a software module comprising processor-executed instructions that are executed by one or more computers, such as a server of a health organization and/or a case manager terminal.

The data receiver module 602 receives data from a database 132. In one embodiment, the data may be information provided in a data input field by a case manager during a patient encounter, where the data was input into the data input field by the case manager and transmitted from the case manager terminal to the database 132. The data is transmitted from the data receiver module 602 to the data link/merge module 604.

Figure 7:
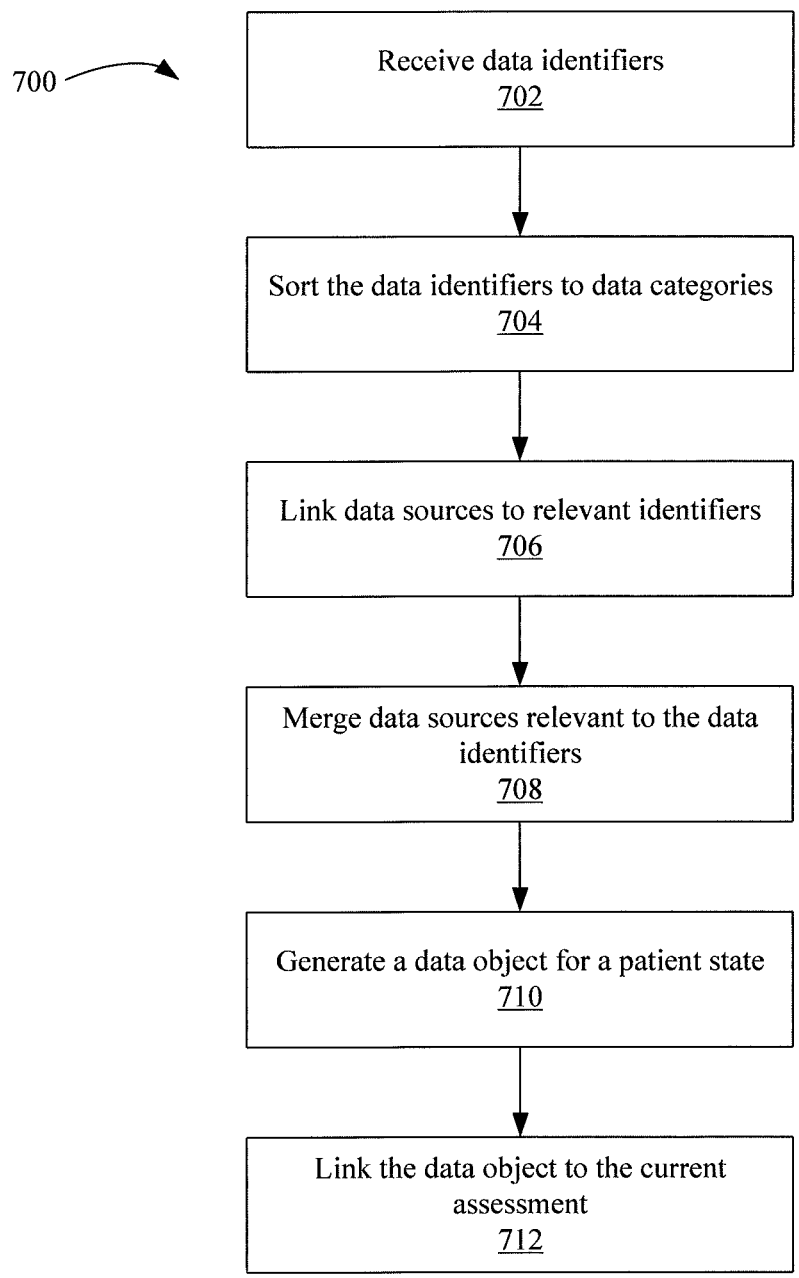
FIG. 7 is a flow diagram of method steps performed by a data link/merge module, according to one embodiment.

FIG. 7 is a flow diagram of method steps performed by a data link/merge module, such as data link/merge module 604 in FIG. 6, according to one embodiment. As shown, the method 700 begins at step 702, where the data link/merge module receives data identifiers. The data identifiers may include identifiers for the data received from the data receiver module 602. In some embodiments, patient data is sorted in categories (e.g., clinical, financial, demographic, etc.) and is merged with reference data. This combined "patient object" is then associated with the appropriate assessment. At step 704, the data link/merge module sorts the data identifiers to data categories. At step 706, the data link/merge module links data sources to relevant identifiers. At step 708, the data link/merge module merges data sources relevant to the data identifiers. At step 710, the data link/merge module generates a data object for a patient state. At step 712, the data link/merge module links the data object to the current assessment.

Figure 8:
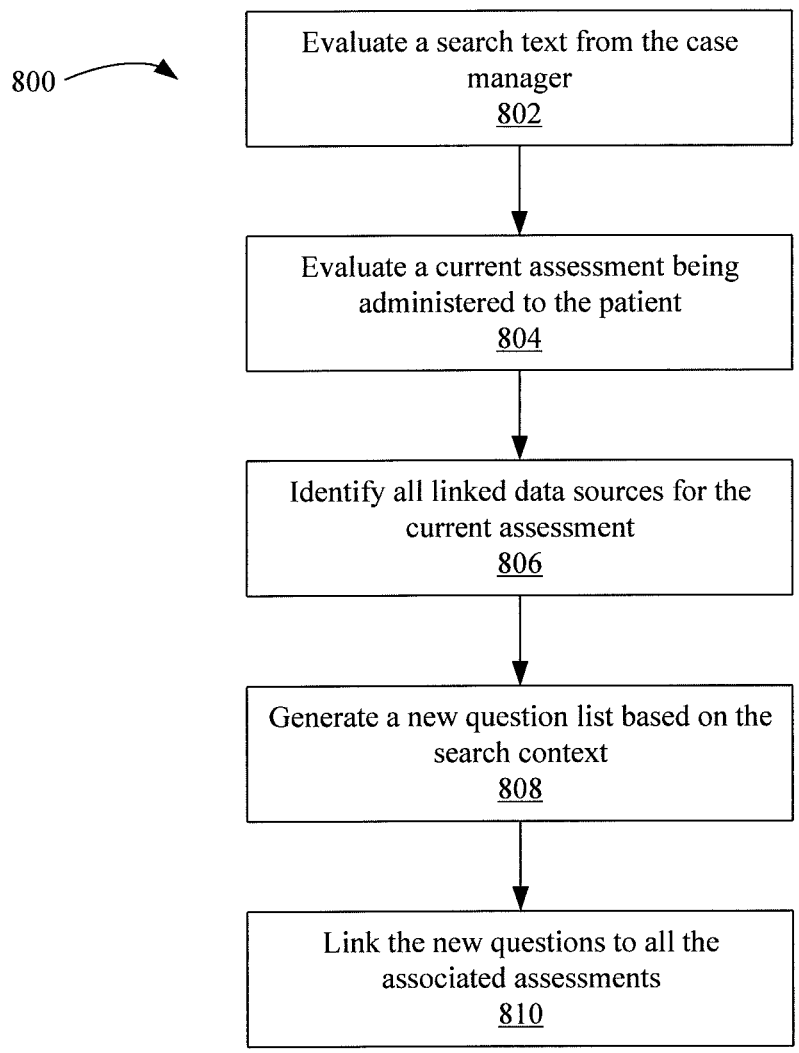
FIG. 8 is a flow diagram of method steps performed by a suggestion module, according to one embodiment.

FIG. 8 is a flow diagram of method steps performed by a suggestion module, such as suggestion module 606 in FIG. 6, according to one embodiment. As shown, the method 800 begins at step 802, where the suggestion module evaluates a search text from the case manager. For example, the search text may be input into the data input field 504 described above. As such, when the conversation between the patient and the case manager shifts to a new topic, the case manager can type free text into the data input field 504. The suggestion module associates the free text with available assessments and generates the next set of questions to present to the case manager. At step 804, the suggestion module evaluates a current assessment being administered to the patient. At step 806, the suggestion module identifies all linked data sources for the current assessment. At step 808, the suggestion module generates a new question list based on the search context. At step 810, the suggestion module links the new questions to all the associated assessments.

Figure 9:
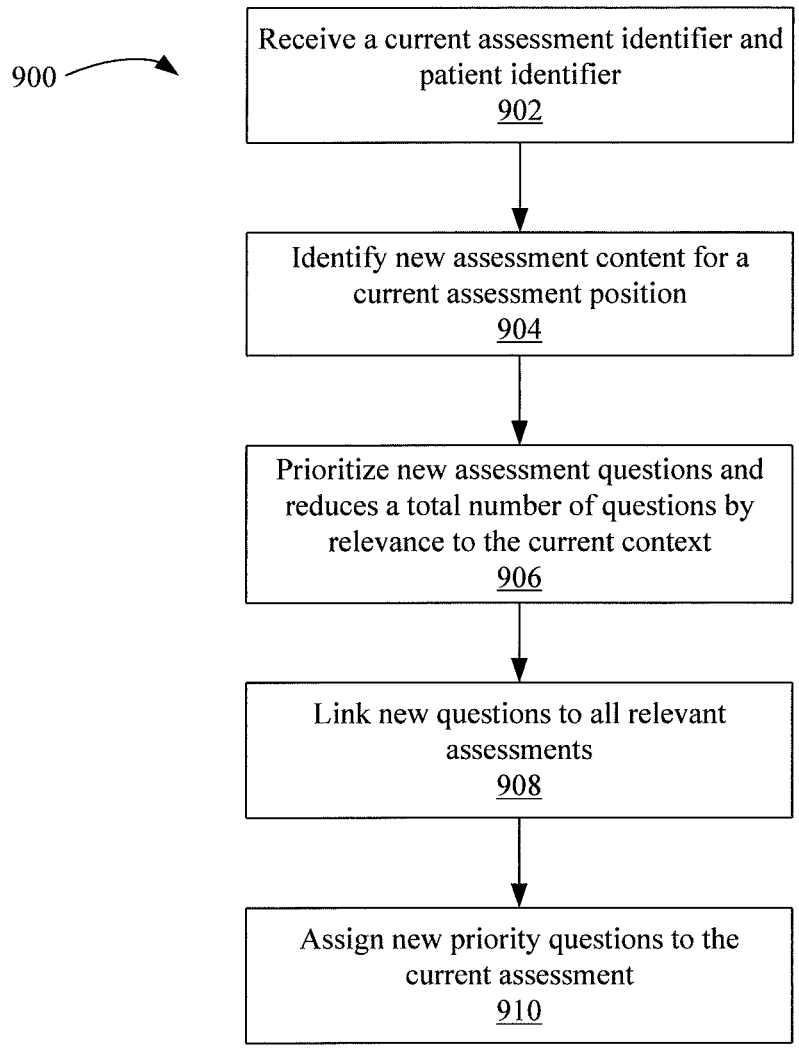
FIG. 9 is a flow diagram of method steps performed by an assessment engine module, according to one embodiment.

FIG. 9 is a flow diagram of method steps performed by an assessment engine module, such as assessment engine module 608 in FIG. 6, according to one embodiment. The assessment engine module is configured to select the next assessment and select the next set of questions to present to the case manager. As shown, the method 900 begins at step 902, where the assessment engine module receives a current assessment identifier and patient identifier. At step 904, the assessment engine module identifies new assessment content for a current assessment position. At step 906, the assessment engine module prioritizes new assessment questions and reduces a total number of questions by relevance to the current context. At step 908, the assessment engine module links new questions to all relevant assessments. At step 910, the assessment engine module assigns new priority questions to the current assessment.

Referring back to FIG. 6, new priority questions from the assessment engine module are transmitted to the assessment view module 610. The assessment view module 610 communicates with the case manager terminal to display the new priority questions in the case manager terminal user interface to the case manager. The new priority questions can be from the same assessment as the prior question or from a different assessment.

Figure 10:
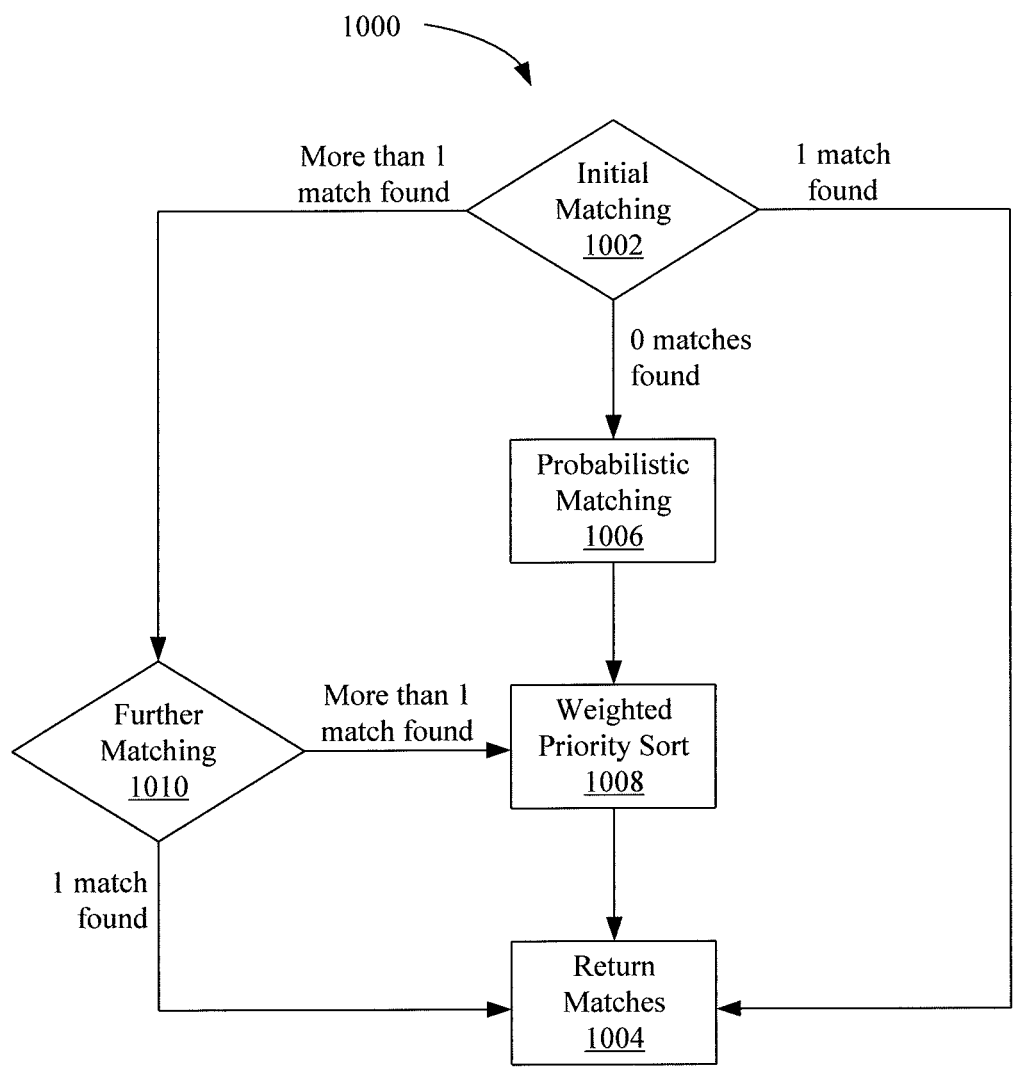
FIG. 10 is a flow diagram of method steps of question and assessment matching, according to one embodiment.

FIG. 10 is a flow diagram of method steps of question and assessment matching, according to one embodiment. In some implementations, based on free text entry by the case manager, different assessments can be selected as being relevant to the free text entry. Certain questions can then the selected as being the appropriate questions to present. FIG. 10 is a visual representation of the background logic presented in FIGS. 8 and 9. As shown, the method 1000 begins at step 1002, where the assessment engine module performs an initial matching of new content to the pool of possible assessment questions. The initial matching may be performed by executing any technically feasible matching algorithm, including deterministic or probabilistic matching algorithms. If exactly one match is found, then the method 1000 proceeds to step 1004, where the assessment engine module returns the one match question.

If at step 1002, zero matches are found, then the method 1000 proceeds to step 1006, where the assessment engine module performs probabilistic matching to determine which remaining assessment questions are left to be answered based on the new content. At step the 1008, the assessment engine module performs a weighted priority sort (e.g., based on severity of conditions, the patient's medical data, and/or unsolicited input from the patient) of the remaining assessment questions are left to be answered. The matches are then returned at step 1004.

If at step 1002, more than one match is found, then the method 1000 proceeds to step 1010, where the assessment engine module performs further matching of the new content to assessment questions. The further matching may be any technically feasible matching algorithm, including deterministic or probabilistic matching. If, at step 1010, exactly one match is found, the method proceeds to step 1004 where the match is returned. If, at step 1010, more than one match is found, then the method 1000 proceeds to step 1008, described above.

Figure 11:
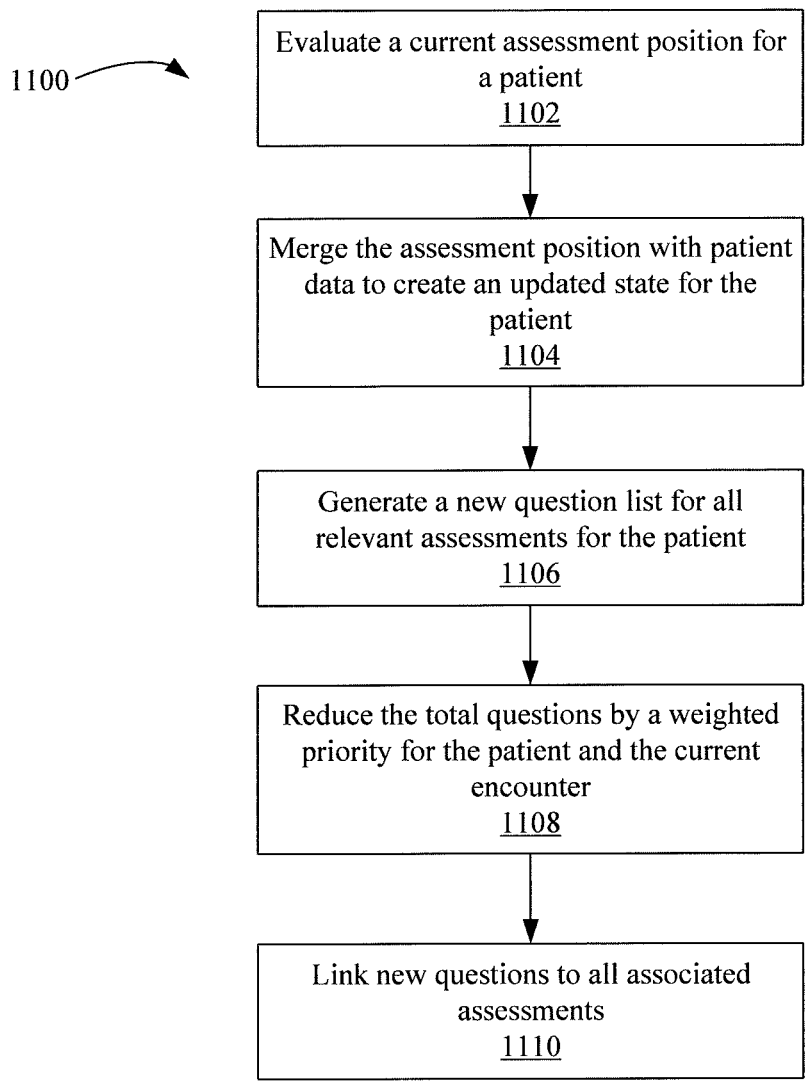
FIG. 11 is a flow diagram of method steps for linking new questions to all associated assessments, according to one embodiment.

FIG. 11 is a flow diagram of method steps for linking new questions to all associated assessments, according to one embodiment. In one implementation, FIG. 11 provides the logic for updating the next set of questions to be presented to the case manager. The intention of this process is to support the case manager in staying on task, making progress towards completing an assessment. As shown, the method 1100 begins at step 1102, where the calculation engine module evaluates a current assessment position for a patient 1102. At step 1104, the calculation engine module merges the assessment position with patient data to create an updated state for the patient. At step 1106, the calculation engine module generates a new question list for all relevant assessments for the patient. At step 1108, the calculation engine module reduces the total questions by a weighted priority for the patient and the current encounter. At step 1110, the calculation engine module links new questions to all associated assessments.

Figure 12A:
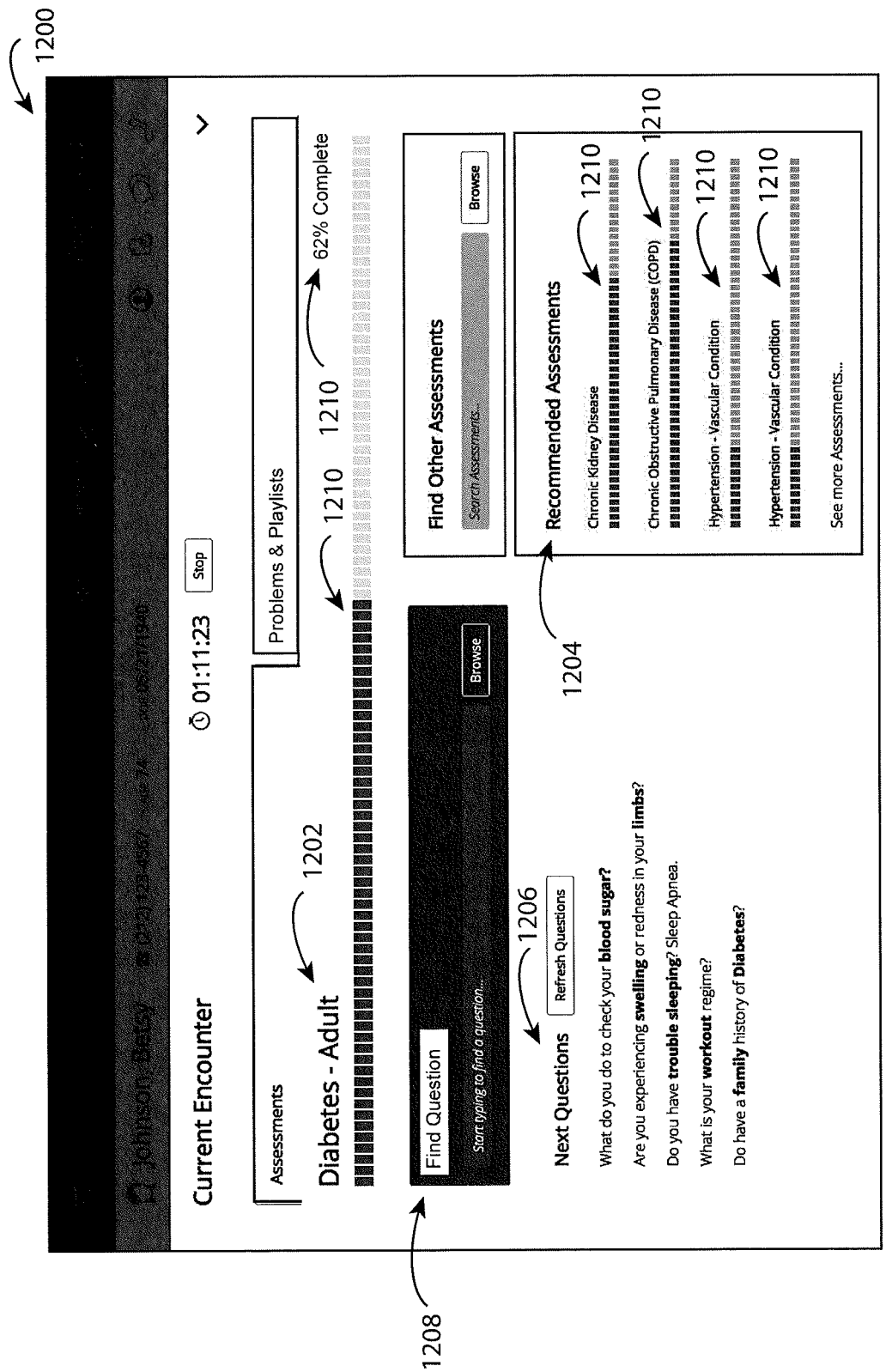
FIGS. 12A-12D are screenshots that illustrate example user interface screens displayed on a case manager terminal while performing a patient encounter, according to some embodiments.

FIGS. 12A-12D are screenshots that illustrate example user interface screens displayed on a case manager terminal while performing a patient encounter, according to some embodiments. As shown in FIG. 12A, a user interface 1200 includes an indicator of a current assessment 1202 (e.g., "Diabetes—Adult") and next questions 1206 to ask the patient for the current assessment 1202. Additional recommended assessments 1204 that are recommended to complete with the patient are also shown in the user interface 1200. Visual indicators 1210 indicate to the case manager a level of completeness (e.g., completion percentage) of the various assessments to be completed and/or recommended to be completed.

Also shown in the user interface 1200 is a data input field 1208 for the case manager to input information to find new questions to ask the patient. As described, the information provided in the data input field 1208 may be information provided by the patient.

In some embodiments, during an assessment, the case manager can follow the scripted next questions 1206 or type a new topic into the data input field 1208 in order to follow the patient's diversion "off-script."

Figure 12B:
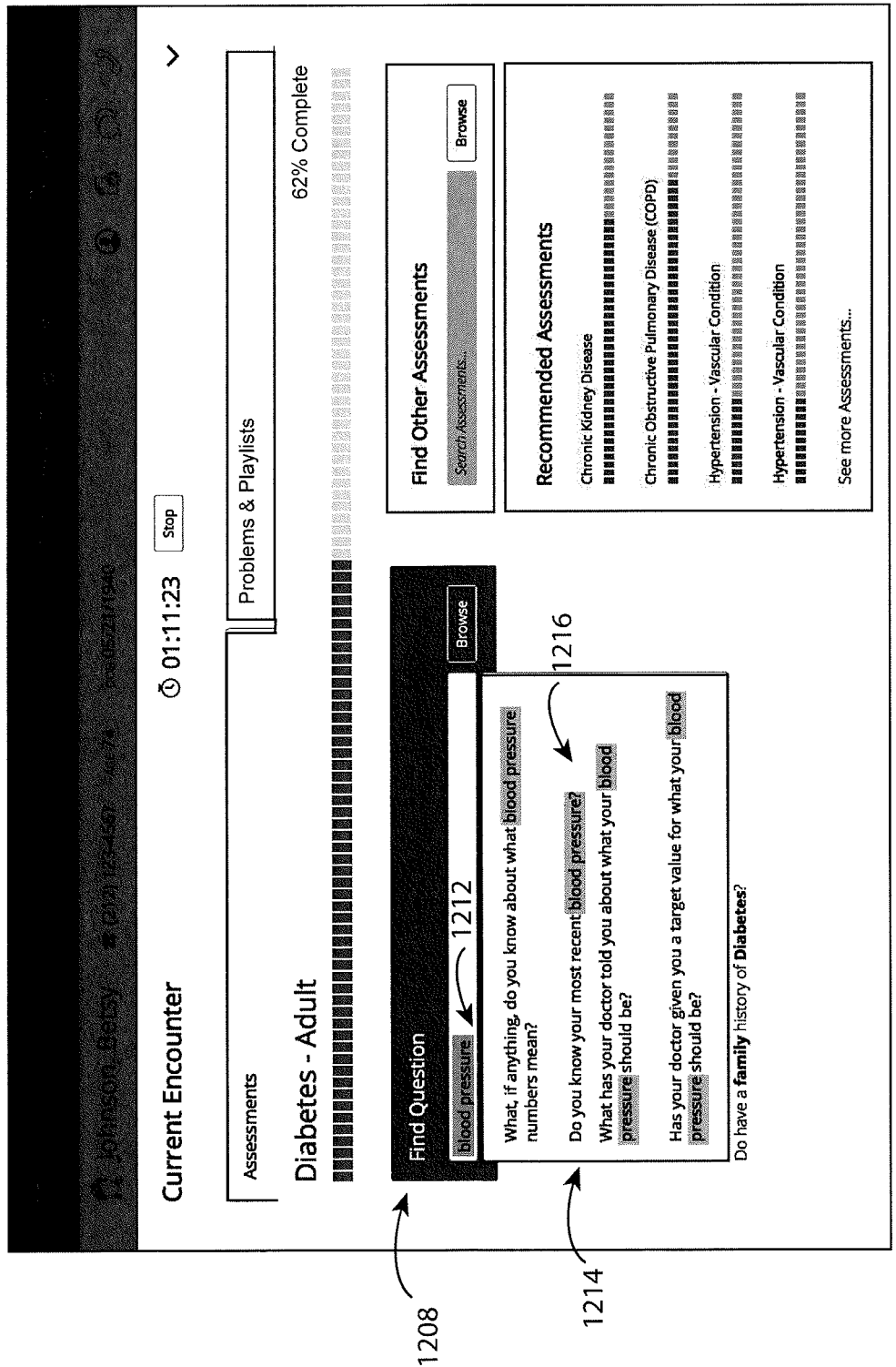

As shown in FIG. 12B, the case manager has input the text 1212 "blood pressure" into the data input field 1208. In response, the user interface is updated to display a listing 1214 of recommended questions to ask the patient based on the text 1212. In some embodiments, the questions displayed in the listing 1214 are helpful toward completing one or more of the assessments being administered or recommended for the patient.

Figure 12C:
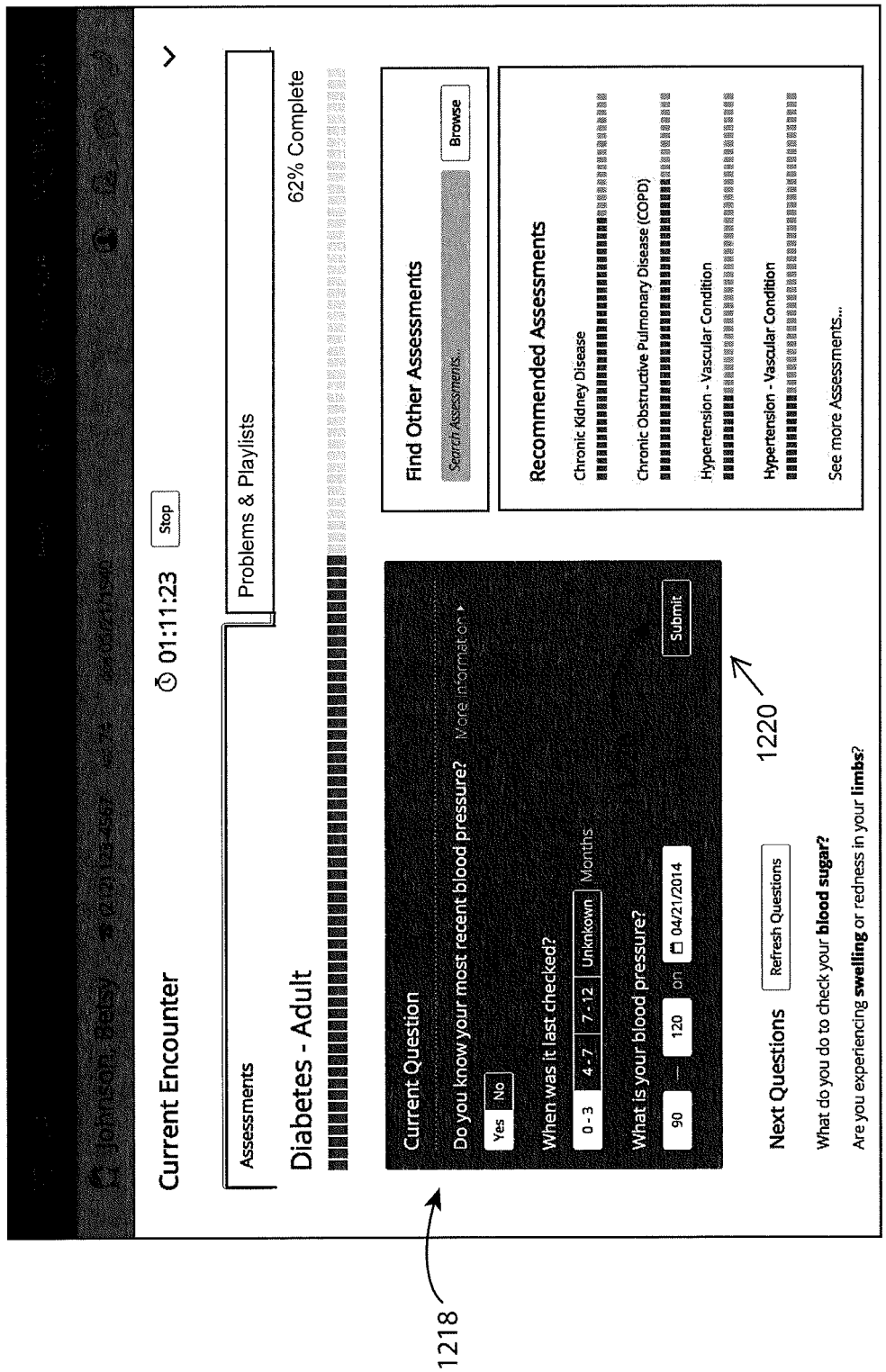

In the example in FIG. 12B, the case manager may select the recommended question 1216 (i.e., "Do you know your most recent blood pressure?"), which causes the user interface shown in FIG. 12C to be displayed. In FIG. 12C, a listing of questions 1218 related to "recent blood pressure" are provided. Once the answers are complete, the case manager can click "Submit" 1220, which causes the user interface shown in FIG. 12D to be displayed.

Figure 12D:
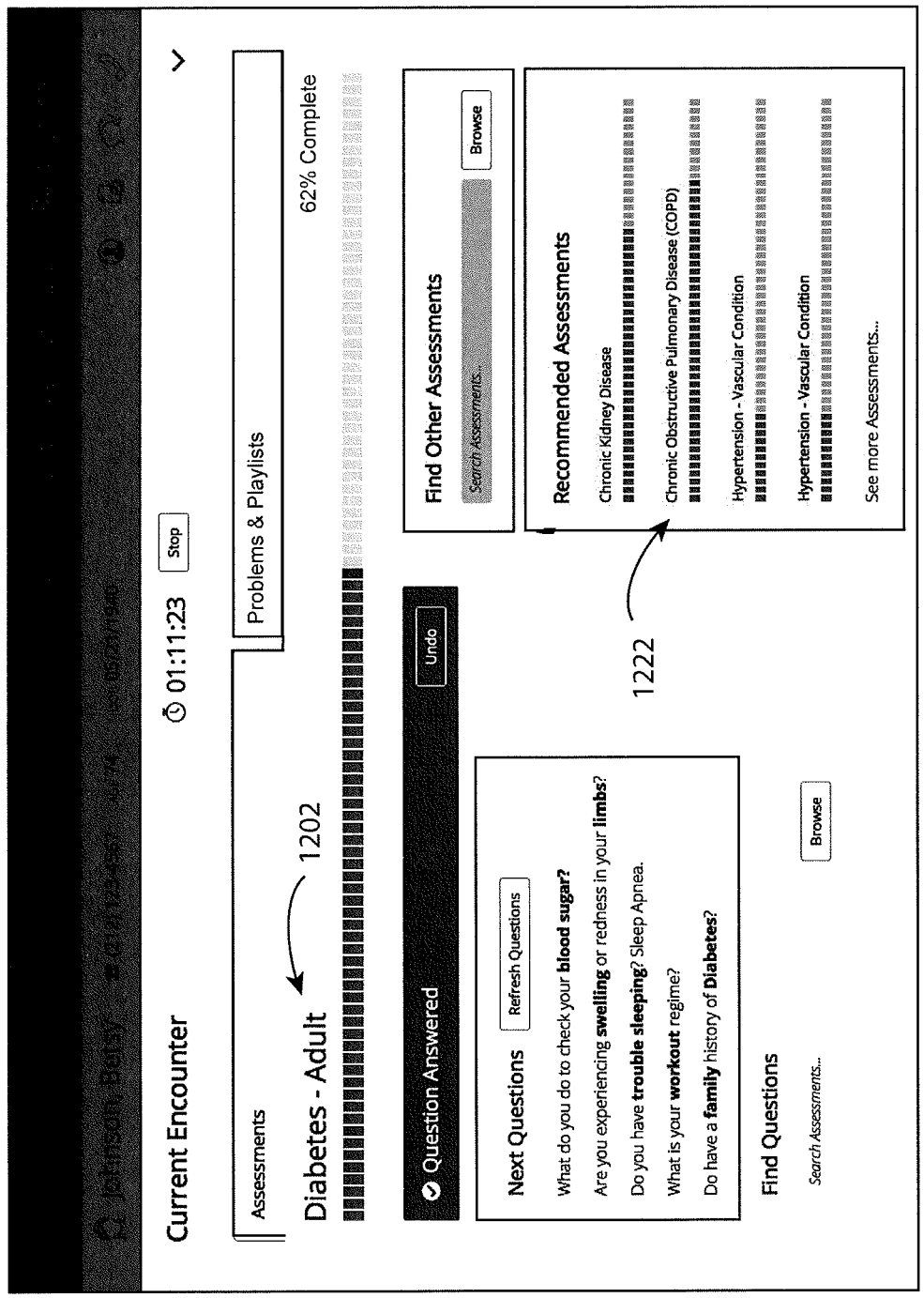

As shown in FIG. 12D, the answer to the blood pressure question(s) increase the completion progress of one of the recommended assessments 1204, namely the "Chronic Obstructive Pulmonary Disease (COPD)" assessment 1222. The current assessment 1202, however, remains as "Diabetes—Adult."

Figure 13:
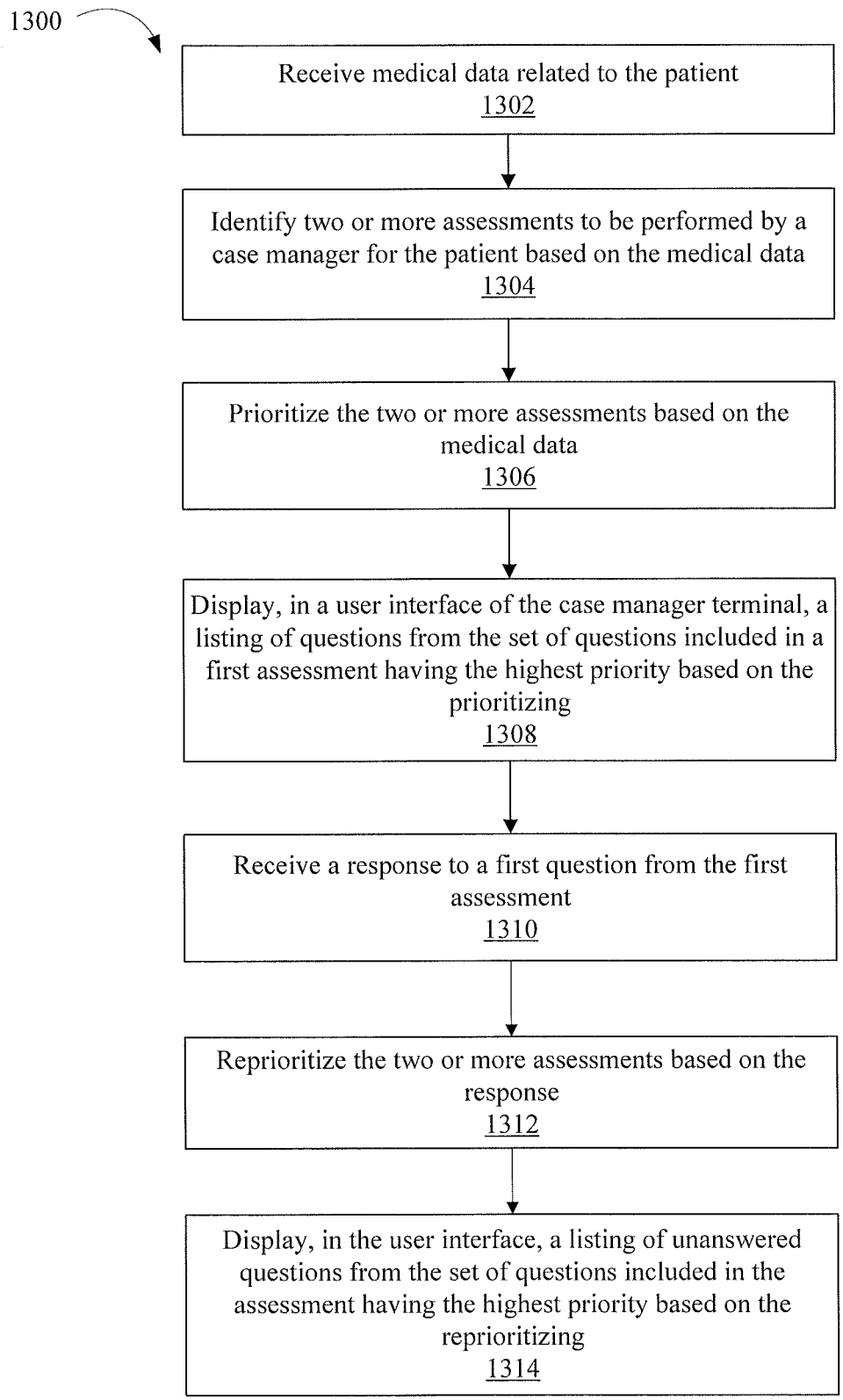
FIG. 13 is a flow diagram of method steps performed by a calculation engine module for performing one or more health assessments, according to one embodiment.

FIG. 13 is a flow diagram of method steps performed by a calculation engine module, such as calculation engine module 126 in FIG. 2, for performing one or more health assessments, according to one embodiment. As shown, the method 1300 begins at step 1302, where the calculation engine module receives medical data related to the patient. In some embodiments, the medical data includes at least claims data and lab data.

At step 1304, the calculation engine module identifies two or more assessments to be performed by a case manager for the patient based on the medical data. In some embodiments, each of said two or more assessments includes a different set of questions to be answered by the patient. Some questions may be included in multiple assessments. Also, in some embodiments, each set of questions is directed to a different medical condition that the system identifies the patient is at risk of having based on the medical data.

At step 1306, the calculation engine module prioritizes the two or more assessments based on the medical data. In some embodiments, the calculation engine module may further consider additional input from the case manager when prioritizing the two or more assessments. The additional input from the case manager may be based on unsolicited input from the patient, such as an amount of time that the patient has to speak with the case manager, or a particular condition that the patient wishes to discuss with the case manager. Also, in some embodiments, the additional input from the case manager is indicative of case manager and/or patient input regarding the prioritization of the assessments. Also, in some embodiments, the additional input may be based on a response to a previous question that was asked to the patient.

At step 1308, the calculation engine module displays, in a user interface of the case manager terminal, a listing of questions from the set of questions included in a first assessment having the highest priority based on the prioritizing.

At step 1310, the calculation engine module receives a response to a first question from the first assessment. At step 1312, the calculation engine module reprioritizes the two or more assessments based on the response. In some embodiments, after reprioritizing, the first assessment may remain the assessment with the highest priority. Alternatively, after reprioritizing, the calculation engine module may identify a different assessment other than the first assessment as having the highest priority. Reprioritizing may be based on additional input additional input from the case manager, such as unsolicited input from the patient in response to the first question (e.g., as an amount of time that the patient has to speak with the case manager, or a particular condition that the patient wishes to discuss with the case manager).

At step 1314, the calculation engine module displays, in the user interface, a listing of unanswered questions from the set of questions included in the assessment having the highest priority based on the reprioritizing. In some embodiments, after reprioritizing, the first assessment may remain the assessment with the highest priority. Alternatively, after reprioritizing, the calculation engine module may identify a different assessment other than the first assessment as having the highest priority.

In sum, embodiments of the disclosure disclose dynamically changing the order of questions, providing follow-up questions based on a patient's response, and/or visually representing the level of completeness of numerous assessments that are simultaneously being completed based on the conversational flow of the assessment. By providing a data input field that can generate new questions to ask the patient, multiple assessments can be completed in parallel, while keeping the conversation relevant to the patient, which keeps the patient engaged and provides for better and faster assessment completion.

Although embodiments of the disclosure provide for a calculation engine module 126 as part of a health plan organization 106, other embodiments may include the calculation engine module 126 as part of a server executed by a health care provider. In some embodiments, any entity that has access to clinical data from the patient's medical record may implement the calculation engine module 126 to perform the features and functions disclosed herein. In still further embodiments, the assessment workflow described herein may implemented outside of the health care industry and is applicable to any industry that involves assessments, such as, for example, the financial assessments (e.g., assessments to determine a person's financial status, credit worthiness, level of credit to offer, set of terms to provide the customer, etc.), academic assessments, online dating or matchmaking assessments, and employment assessments, among others.

All references, including publications, patent applications and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

One embodiment of the disclosure may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A computing device, comprising:
an electronic display device;
one or more memories; and
one or more processors, wherein the one or more processors are configured to execute instructions stored in the one or more memories to perform steps of:
receiving, from a server computing device, medical data related to a patient and stored in a clinical data database;
identifying plural medical conditions for the patient from the medical data;
from the medical data, identifying plural assessments corresponding to the plural identified medical conditions, respectively, wherein each of said assessments includes a set of questions tailored to the respective one of the plural medical conditions;
performing a weighted analysis of the medical data and, based on the weighted analysis, prioritizing said assessments relative to each other and prioritizing the questions within each assessment;
based on the weighted analysis of the medical data, selecting a top prioritized assessment, and a top prioritized question from the top prioritized assessment, for presentation by a case manager and response by the patient, wherein the top prioritized assessment is directed to a first medical condition;
displaying, on the electronic display device, a first graphical user interface (GUI) screen, wherein the first GUI screen includes a first GUI portion that displays, in an assessments tab of the first GUI portion, an identifier for the top prioritized assessment corresponding to the first medical condition, a second GUI portion that displays the top prioritized question from the top prioritized assessment, a third GUI portion that displays a listing of assessments from the plural assessments other than the top prioritized assessment, and a fourth GUI portion that includes a free text data input field, wherein the listing of assessments includes visual indicators corresponding to a completeness of each assessment displayed in the third GUI portion;
receiving a response from the patient to the top prioritized question, wherein the response from the patient is indicative of a particular medical condition that the patient has provided as a topic that the patient is interested in discussing, wherein the response from the patient is directed to a medical condition other than the first medical condition, and wherein data corresponding to the response from the patient is entered by the case manager into the free text data input field of the fourth GUI portion;
based on both the medical data and the data corresponding to the response from the patient that is entered by the case manager into the free text data input field of the fourth GUI portion, reprioritizing said plural assessments based on a weighted analysis of both the medical data and the data corresponding to the response from the patient;
based on the weighted analysis of both the medical data and the data corresponding to the response from the patient, selecting a top prioritized uncompleted assessment after reprioritizing said plural assessments and a top prioritized unanswered question therein, wherein the top prioritized uncompleted assessment after reprioritizing is directed to a second medical condition, wherein the top prioritized assessment corresponding to the first medical condition after prioritizing said assessments based on the medical data is different than the top prioritized uncompleted assessment after reprioritizing said assessments based on the medical data and the data corresponding to the response from the patient; and displaying, on the electronic display device, a second GUI screen, wherein the second GUI screen includes a first GUI portion that displays, in an assessments tab of the first GUI portion, an identifier for the top prioritized uncompleted assessment after reprioritizing corresponding to the second medical condition, a second GUI portion that displays the top prioritized question from the top prioritized uncompleted assessment after reprioritizing, a third GUI portion that displays a listing of assessments from the plural assessments other than the top prioritized uncompleted assessment after reprioritizing, and a fourth GUI portion that includes a free text data input field, wherein the listing of assessments includes visual indicators corresponding to a completeness of each assessment displayed in the third GUI portion.

2. The computing device of claim 1, wherein the response from the patient is indicative of an amount of time that the patient has to speak with the case manager.

3. The computing device of claim 1, wherein each of the plural assessments includes mutually unique sets of questions to be answered by the patient.

4. A method, comprising:
receiving, by a processor from a server computing device, medical data related to a patient and stored in a clinical data database;
identifying, by the processor, plural medical conditions for the patient from the medical data;
from the medical data, identifying, by the processor, plural assessments corresponding to the plural identified medical conditions, respectively, wherein each of said assessments includes a set of questions tailored to the respective one of the plural medical conditions;
performing, by the processor, a weighted analysis of the medical data and, based on the weighted analysis, prioritizing said assessments relative to each other and prioritizing the questions within each assessment;
based on the weighted analysis of the medical data, selecting, by the processor, a top prioritized assessment, and a top prioritized question from the top prioritized assessment, for presentation by a case manager and response by the patient, wherein the top prioritized assessment is directed to a first medical condition;
displaying, on an electronic display device, a first graphical user interface (GUI) screen, wherein the first GUI screen includes a first GUI portion that displays, in an assessments tab of the first GUI portion, an identifier for the top prioritized assessment corresponding to the first medical condition, a second GUI portion that displays the top prioritized question from the top prioritized assessment, a third GUI portion that displays a listing of assessments from the plural assessments other than the top prioritized assessment, and a fourth GUI portion that includes a free text data input field, wherein the listing of assessments includes visual indicators corresponding to a completeness of each assessment displayed in the third GUI portion;

receiving, by the processor, a response from the patient to the top prioritized question, wherein the response from the patient is indicative of a particular medical condition that the patient has provided as a topic that the patient is interested in discussing, wherein the response from the patient is directed to a medical condition other than the first medical condition, and wherein data corresponding to the response from the patient is entered by the case manager into the free text data input field of the fourth GUI portion;

based on both the medical data and the data corresponding to the response from the patient that is entered by the case manager into the free text data input field of the fourth GUI portion, reprioritizing, by the processor, said plural assessments, based on a weighted analysis of both the medical data and the data corresponding to the response from the patient;

based on the weighted analysis of both the medical data and the data corresponding to the response from the patient, selecting, by the processor, a top prioritized uncompleted assessment after reprioritizing said plural assessments and a top prioritized unanswered question therein, wherein the top prioritized uncompleted assessment after reprioritizing is directed to a second medical condition, wherein the top prioritized assessment corresponding to the first medical condition after prioritizing said assessments based on the medical data is different than the top prioritized uncompleted assessment after reprioritizing said assessments based on the medical data and the data corresponding to the response from the patient; and displaying, on the electronic display device, a second GUI screen, wherein the second GUI screen includes a first GUI portion that displays, in an assessments tab of the first GUI portion, an identifier for the top prioritized uncompleted assessment after reprioritizing corresponding to the second medical condition, a second GUI portion that displays the top prioritized question from the top prioritized uncompleted assessment after reprioritizing, a third GUI portion that displays a listing of assessments from the plural assessments other than the top prioritized uncompleted assessment after reprioritizing, and a fourth GUI portion that includes a free text data input field, wherein the listing of assessments includes visual indicators corresponding to a completeness of each assessment displayed in the third GUI portion.

5. The method of claim 4, wherein the response from the patient is indicative of an amount of time that the patient has to speak with the case manager.

6. The method of claim 4, wherein each of the plural assessments includes mutually unique sets of questions to be answered by the patient.

7. A non-transitory computer-readable storage medium storing instructions that, when executed by a processor, cause a computer system to perform the steps of:
receiving, from a server computing device, medical data related to a patient and stored in a clinical data database;
identifying plural medical conditions for the patient from the medical data;
from the medical data, identifying plural assessments corresponding to the plural identified medical conditions, respectively, wherein each of said assessments includes a set of questions tailored to the respective one of the plural medical conditions;

performing a weighted analysis of the medical data and, based on the weighted analysis, prioritizing said assessments relative to each other and prioritizing the questions within each assessment;

based on the weighted analysis of the medical data, selecting a top prioritized assessment, and a top prioritized question from the top prioritized assessment, for presentation by a case manager and response by the patient, wherein the top prioritized assessment is directed to a first medical condition;

displaying, on an electronic display device, a first graphical user interface (GUI) screen, wherein the first GUI screen includes a first GUI portion that displays, in an assessments tab of the first GUI portion, an identifier for the top prioritized assessment corresponding to the first medical condition, a second GUI portion that displays the top prioritized question from the top prioritized assessment, a third GUI portion that displays a listing of assessments from the plural assessments other than the top prioritized assessment, and a fourth GUI portion that includes a free text data input field, wherein the listing of assessments includes visual indicators corresponding to a completeness of each assessment displayed in the third GUI portion;

receiving a response from the patient to the top prioritized question, wherein the response from the patient is indicative of a particular medical condition that the patient has provided as a topic that the patient is interested in discussing, wherein the response from the patient is directed to a medical condition other than the first medical condition, and wherein data corresponding to the response from the patient is entered by the case manager into the free text data input field of the fourth GUI portion;

based on both the medical data and the data corresponding to the response from the patient that is entered by the case manager into the free text data input field of the fourth GUI portion, reprioritizing said plural assessments, based on a weighted analysis of both the medical data and the data corresponding to the response from the patient;

based on the weighted analysis of both the medical data and the data corresponding to the response from the patient, selecting a top prioritized uncompleted assessment after reprioritizing said plural assessments and a top prioritized unanswered question therein, wherein the top prioritized uncompleted assessment after reprioritizing is directed to a second medical condition, wherein the top prioritized assessment corresponding to the first medical condition after prioritizing said assessments based on the medical data is different than the top prioritized uncompleted assessment after reprioritizing said assessments based on the medical data and the data corresponding to the response from the patient; and displaying, on the electronic display device, a second GUI screen, wherein the second GUI screen includes a first GUI portion that displays, in an assessments tab of the first GUI portion, an identifier for the top prioritized uncompleted assessment after reprioritizing corresponding to the second medical condition, a second GUI portion that displays the top prioritized question from the top prioritized uncompleted assessment after reprioritizing, a third GUI portion that displays a listing of assessments from the plural assessments other than the top prioritized uncompleted assessment after reprioritizing, and a fourth GUI portion that includes a free text data input field, wherein the listing of assessments includes visual indicators corresponding to a completeness of each assessment displayed in the third GUI portion.

8. The computer-readable storage medium of claim 7, wherein the response from the patient is indicative of an amount of time that the patient has to speak with the case manager.

9. The computer-readable storage medium of claim 7, wherein each of the plural assessments includes mutually unique sets of questions to be answered by the patient.

* * * * *